United States Patent [19]
Dai et al.

[11] Patent Number: 5,792,890
[45] Date of Patent: Aug. 11, 1998

[54] METHOD FOR THE PURIFICATION OF TERTIARY BUTYL ALCOHOL FOR USE IN THE MANUFACTURE OF METHYL TERTIARY BUTYL ETHER

[75] Inventors: Pei-Shing Eugene Dai; Laurence Darrel Neff; Kyle Lee Preston, all of Port Arthur; Rei-Yu Judy Hwan, Sugar Land; John Frederick Knifton, Austin, all of Tex.

[73] Assignee: Huntsman Specialty Chemicals Corp., Austin, Tex.

[21] Appl. No.: 792,033

[22] Filed: Feb. 3, 1997

[51] Int. Cl.$^6$ .................................... C07C 41/09
[52] U.S. Cl. .................... 568/697; 568/698; 568/910
[58] Field of Search .................... 568/697, 698, 568/910

[56] References Cited

U.S. PATENT DOCUMENTS 4,296,263  10/1981  Worrell et al. .................... 568/910
5,243,091   9/1993  Kruse et al. ...................... 568/697
5,354,912  10/1994  Hwan et al. ...................... 568/697

*Primary Examiner*—Gary Geist
*Assistant Examiner*—Sreeni Padmanabhan
*Attorney, Agent, or Firm*—Russell R. Stolle; Carl G. Ries

[57] ABSTRACT

A tertiary butyl alcohol charge stock contaminated with from about 0.5 to about 2 wt. % of corrosive oxygen-containing impurities, including peroxides and formates, is passed through an oxygenates decomposition reactor containing a bed of a basic zeolite catalyst to decompose the peroxides and oxygen-containing impurities, including peroxides and formates, and to dehydrate a portion of the tertiary butyl alcohol to form isobutylene and water to form a substantially less-corrosive tertiary butyl alcohol feedstock that is substantially free from oxygen-containing impurities, including formates that is suitable for reaction with methanol in a methyl tertiary butyl ether etherification reactor to form a methyl tertiary butyl ether etherification reaction product from which methyl tertiary butyl ether can be recovered.

10 Claims, 1 Drawing Sheet

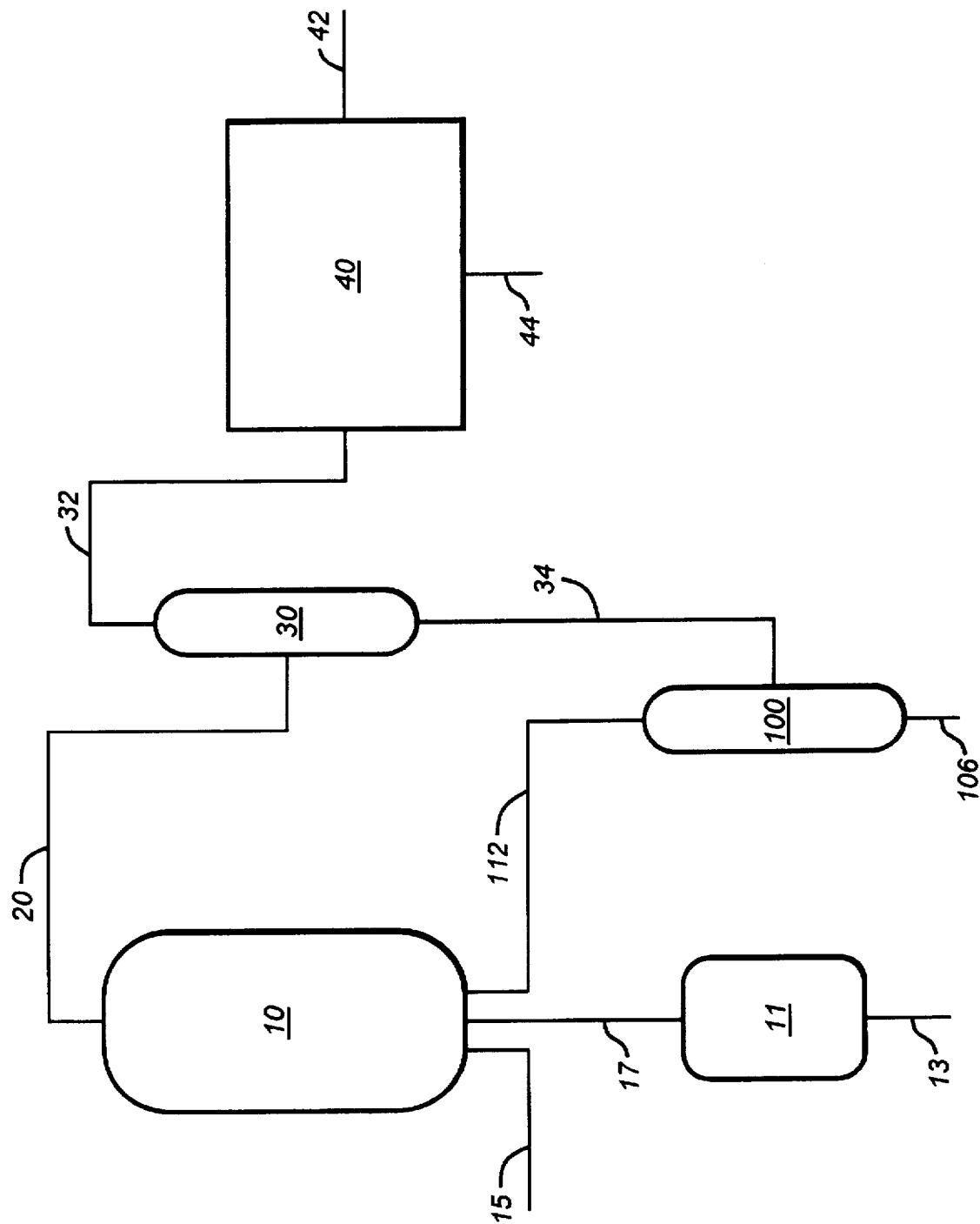

5,792,890

1

METHOD FOR THE PURIFICATION OF TERTIARY BUTYL ALCOHOL FOR USE IN THE MANUFACTURE OF METHYL TERTIARY BUTYL ETHER

BACKGROUND OF THE INVENTION

1. Technical Field of the Invention

This invention relates to the purification of tertiary butyl alcohol for use in the manufacture of methyl tertiary butyl ether. More particularly, this invention relates to a method for the substantially complete removal of oxygen-containing impurities, including peroxides and tertiary butyl formate contained in contaminated tertiary butyl alcohol by contacting the contaminated tertiary butyl alcohol with a basic zeolite catalyst.

Methyl tert-butyl ether is useful as a blending component in high octane gasoline.

2. Prior Art

Worrell U.S. Pat. No. 4,296,263 discloses the oxidation of isobutane with air to provide to tertiary butyl alcohol and tertiary butyl hydroperoxide. It is disclosed that the reaction product, a solution of tertiary butyl hydroperoxide in tertiary butyl alcohol, contains minor amounts of oxygen-containing by-products such as acetic acid, formic acid and esters thereof that are purged from the system during purification of the reaction product.

A number of catalysts have been proposed for the decomposition of tertiary butyl hydroperoxide in solution in tertiary butyl alcohol to form additional tertiary butyl alcohol including cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The tertiary butyl alcohol reaction product derived from tertiary butyl hydroperoxide in this manner will be contaminated with oxygen-containing impurities.

Processes for the manufacture of methyl tertiary butyl ether from tertiary butyl alcohol and methanol are known, as illustrated, for example, by Kruse et al. U.S. Pat. No. 5,243,091, Gupta U.S. Pat. No. 5,292,964, Hwan et al. U.S. Pat. No. 5,354,912, Kruse et al. U.S. Pat. No. 5,386,065, Kruse et al. U.S. Pat. No. 5,387,721 and Cassata et al. U.S. Pat. No. 5,395,982. In the practice of these processes, the tertiary butyl alcohol feedstock is passed through a peroxides decomposition reactor before being charged to an etherification reactor together with methanol for the formation of methyl tertiary butyl ether.

For example, Kruse et al. U.S. Pat. No. 5,243,091 discloses a method for the preparation of methyl tertiary butyl ether wherein the tertiary butyl alcohol is initially charged to a peroxides decomposition zone, which is preferably a thermal decomposition zone. When the peroxides are to be thermally decomposed, the peroxides-contaminated tertiary butyl alcohol feedstock is conventionally passed through a peroxides decomposition reactor at a temperature of about 100° to about 200° C., a pressure of about 80 to about 500 psia at a flow rate of about 0.5 to 20 volumes of feedstock per reactor volume per hour to thereby provide a substantially peroxides-free tertiary butyl alcohol reaction product. The thus-treated tertiary butyl alcohol, which will still contain oxygen-containing impurities such as tertiary butyl formate, is then mixed with methanol and the mixture is catalytically reacted to form an etherification reaction product comprising unreacted methanol, unreacted tertiary butyl alcohol, water, isobutylene methyl tertiary butyl ether, and oxygen-containing impurities present in the tertiary butyl alcohol feedstock. Methyl tertiary butyl ether is recovered from the reaction mixture.

Sanderson et al. U.S. Pat. No. 5,354,917 discloses a method wherein an isobutane oxidation product comprising a solution of 5 to 30 wt. % of tertiary butyl hydroperoxide in tertiary butyl alcohol is brought into contact with a catalyst consisting of alumina or carbon having rhodium deposited thereon in order to convert the tertiary butyl hydroperoxide to decomposition products, principally tertiary butyl alcohol. Sanderson et al. specify reaction conditions including a temperature of about 25° to about 250° C. and a pressure of about 0 to 1000 psig, with a temperature of about 40° to about 150° C. and a pressure of about 0 psig being preferred. Tertiary butyl alcohol is recovered from the decomposition products but will be contaminated with minor amounts of oxygen-containing impurities including peroxides and formates. As a consequence, if a tertiary butyl alcohol feedstock prepared by the Sanderson et al. process is to be used in the preparation of methyl tertiary butyl ether, the feedstock must be treated in a preliminary peroxides decomposition zone for the decomposition of the peroxide impurities.

A variety of other catalysts may be used to treat a tertiary butyl alcohol feedstock contaminated with peroxide impurities, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

SUMMARY OF THE INVENTION

When tertiary butyl alcohol is prepared by the oxidation of isobutane and/or tertiary butyl hydroperoxide, the tertiary butyl alcohol reaction product will contain minor amounts of contaminants such as tertiary butyl hydroperoxide, ditertiary butyl peroxide, allyl tertiary butyl peroxide, etc., and will also contain minor amounts of oxygen-containing contaminants including acetone, isopropyl alcohol, dimethyl ether, etc., and acidic by-products such as acetic acid, formic acid and esters thereof, including methyl formate and tertiary butyl formate. The contaminated tertiary butyl alcohol charge stock prepared in this fashion is conventionally passed through a peroxides decomposition reactor to prepare a tertiary butyl alcohol feedstock that is fed to a methyl tertiary butyl ether etherification reactor together with methanol to provide the methyl tertiary butyl ether etherification product substantially free from peroxide impurities. The thus-treated tertiary butyl alcohol will still contain a minor amount of oxygen-containing impurities, such as acetone, isopropyl alcohol and dimethyl ether and also formate esters such as formic acid, methyl formate and tertiary butyl formate. Thereafter, during the reaction of tertiary butyl alcohol with methanol to form a reaction product containing methyl tertiary butyl ether and during the work-up of the reaction product, the oxygen-containing impurities, and especially the formate esters can be converted to form by-products including corrosive acidic by-products such as formic acid, thus creating a severe corrosion problem.

These and other related problems are resolved through the process of the present invention wherein a tertiary butyl alcohol charge stock contaminated with from about 0.5 to about 2 wt. % of oxygen-containing impurities, including peroxides and formates, is passed through an oxygenates decomposition reactor containing a bed of a basic zeolite catalyst at a temperature of about 120° to about 260° C. to decompose the peroxides and oxygen-containing impurities, including formates, and to form a tertiary butyl alcohol feedstock that is substantially free from such impurities as evidenced by the low tertiary butyl formate content of the reaction product, for example, in the range of about 0.001 to about 0.01 wt. % of tertiary butyl formate. The present invention permits a significant portion of the tertiary butyl alcohol to be dehydrated in the oxygenates reactor to form isobutylene. The present invention also permits a significant portion of the tertiary butyl alcohol to be dehydrated in the oxygenates decomposition reactor. It also provides a method for producing high purity isobutylene. The thus-produced isobutylene also reacts with methanol to form methyl tertiary butyl ether in the etherification reactor. The dehydration of tertiary butyl alcohol will not present a problem for an existing MTBE manufacturing unit provided that the excess water in the effluent from the oxygenates decomposition reactor is removed by adding a gas/liquid separation device before the effluent is charged to the etherification reactor. The methyl tertiary butyl ether prepared by reacting isobutylene and methanol will be essentially free from oxygenates impurities. Therefore it will further alleviate the corrosion problem to the downstream processing units. Accordingly, the thus-prepared less-corrosive tertiary butyl alcohol feedstock is suitable for reaction with methanol in a methyl tertiary butyl ether etherification reactor to form a substantially less-corrosive methyl tertiary butyl ether reaction product from which methyl tertiary butyl ether can be recovered.

DESCRIPTION OF PREFERRED EMBODIMENTS

In accordance with a preferred embodiment of the present invention, a method for the continuous preparation of methyl tertiary butyl ether (MTBE) from tertiary butyl alcohol (TBA) and methanol (MeOH) is provided comprising the steps of:

a) continuously charging a tertiary butyl alcohol charge stock contaminated with from about 0.5 to about 2 wt. % of oxygen-containing impurities, including peroxides and formates to an oxygenates-decomposition reactor containing a basic zeolite decomposition catalyst and substantially completely decomposing the oxygen-containing contaminants therein to form a substantially non-corrosive tertiary butyl alcohol feedstock comprising tertiary butyl alcohol and isobutylene that is substantially free from peroxide and formate contaminants.

b) continuously charging a reaction feed mixture comprising methanol and the substantially less-corrosive tertiary butyl alcohol feedstock to an etherification reactor containing a bed of an etherification catalyst and reacting the reaction feed mixture therein to form a non-corrosive etherification reaction product comprising unreacted methanol, unreacted tertiary butyl alcohol, water, isobutylene and methyl tertiary butyl ether.

c) continuously charging the etherification reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water.

d) continuously charging the first lower boiling distillation fraction to a methyl tertiary butyl ether processing zone for the formation of additional methyl tertiary butyl ether from the methanol and isobutylene contained therein and for the recovery of methyl tertiary butyl ether; and e) continuously charging the fist higher boiling distillation fraction to a tertiary butyl alcohol recovery distillation zone and separating it therein into a lower boiling tertiary butyl alcohol recycle fraction and a higher boiling water fraction.

Under high temperature (>160° C.) a significant portion of the tertiary butyl alcohol is dehydrated in the oxygenates decomposition reactor to form isobutylene and water. When the water content is greater than 10 wt. %, the effluent from the oxygenates decomposition reactor is continuously charged to a gas and liquid stabilizer zone (which may be either a distillation column or a liquid/liquid separator) and separated therein into gas products comprising primarily isobutylene and small amounts of other non-condensible gases such as methane, carbon monoxide, hydrogen and carbon dioxide and a liquid fraction containing water and tertiary butyl alcohol. Therefore the preferred embodiment may include the additional steps of:

f) charging the effluent from the oxygenates decomposition reactor to a gas and liquid stabilizing zone to provide a gaseous product comprising methane, carbon monoxide, hydrogen and carbon dioxide and a liquid fraction containing water and tertiary butyl alcohol;

g) the gaseous product is charged to a methyl tertiary butyl etherification reactor, as described in b), supra, or is optionally charged to a methyl tertiary butyl ether processing zone as described in d), supra, for the formation of methyl tertiary butyl ether from the reaction of methanol and isobutylene contained therein; and h) the liquid fraction is charged to a tertiary butyl alcohol recovery distillation zone, as described in e), supra, and separated therein into water and a tertiary butyl alcohol recycle fraction.

DETAILED DESCRIPTION OF THE PRESENT INVENTION

Peroxide Decomposition It is known to prepare tertiary butyl alcohol by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. A tertiary butyl alcohol charge stock derived from tertiary butyl hydroperoxide in this manner will be contaminated with oxygen-containing impurities. A typical charge stock prepared in this fashion will contain from about 95 to 98 wt. % of tertiary butyl alcohol and about 2 to about 5 wt. % of oxygen-containing contaminants including tertiary butyl hydroperoxide, ditertiary butyl peroxide, acetone, methyl formate, tertiary butyl formate, isopropyl alcohol, dimethyl ether, etc.

In accordance with the present invention, a tertiary butyl alcohol charge stock containing oxygen-containing contaminants is fed to an oxygenates-decomposition reactor containing a bed of a basic zeolite catalyst, where the oxygen-containing contaminants are substantially completely catalytically decomposed. Reaction conditions to be used include a temperature of about 220° to about 240° C., a pressure of about 80 to about 500 psia at a flow rate of about 0.5 to 20 volumes of charge stock per reactor volume per hour to thereby provide a tertiary butyl alcohol feedstock substantially completely free from oxygen-containing impurities.

The effluent from the oxygenates-decomposition reactor will typically comprise about 95 to about 99 wt. % of a mixture of tertiary butyl alcohol with isobutylene and will contain less than about 0.1 wt. % of oxygen-containing contaminants.

The Oxygenates-Decomposition Catalyst

The oxygenates-decomposition catalyst to be used in accordance with the present invention is a basic zeolite catalyst consisting essentially of a zeolite having about 1 to about 15 wt. % of an alkali metal or an alkaline earth metal Group IA or IIA oxide deposited thereon.

Representative Group IA and IIA alkali metal and alkaline earth metal oxides that can be used include cesium oxide, calcium oxide, barium oxide, etc. Representative zeolites that may be used include large pore zeolites such as Y-zeolites, beta zeolites, mordenite, and silica-aluminophosphates, such as SAPO-31, SAPO-37, and medium pore zeolites such as ZSM-5, ZSM-11 and SAPO-11.

Reaction conditions to be used include a temperature of about 250° to about 500° F. (about 120° to about 260° C.), a pressure of about 100 to about 600 psi and a liquid hourly space velocity (LHSV) of about 0.1 to about 10 volumes of feed per volume of catalyst per hour.

The Etherification Reaction Catalyst

In accordance with the MTBE manufacture and purification method of the present invention, an etherification reactor containing a bed of etherification catalyst is utilized. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Zeolites as disclosed in Japanese Patent 0007432 or aluminosilicate zeolites such as those disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed in the prior art include a reaction temperature of about 90° to about 140° C., a pressure of about 30 to about 500 psia and a space velocity of about 0.5 to about 20 volumes of feed per volume of etherification catalyst per hour.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

The tertiary butyl alcohol charge stock which is contaminated with oxygen-containing impurities is initially charged by way of a tertiary butyl alcohol charge line 13 to an oxygenates-decomposition reactor 11, containing a bed of a basic zeolite decomposition catalyst which is operated at a temperature of about 250° to about 500° F., a pressure of about 100 to about 600 psi and a flow rate of about 0.1 to 10 volumes of feedstock per reactor volume per hour to thereby provide a water-containing tertiary butyl alcohol reaction product comprising a mixture of tertiary butyl alcohol and isobutylene that is substantially free from oxygen-containing contaminants.

The substantially oxygenates-free tertiary butyl alcohol reaction product is continuously discharged from the oxygenates decomposition reactor 11 by a discharge line 17 leading to an etherification reactor 10. Fresh methanol is continuously charged to etherification reactor 10 by a line 15, as is a recycle stream 112 containing recycle methanol and recycle tertiary butyl alcohol. The flow of methanol and tertiary butyl alcohol to the etherification reactor 10 through the lines 15, 17 and 112 is regulated so that a molar excess of methanol is present in the etherification reactor 10, such as, for example, a molar ratio of about 1.1 to about 3 moles of methanol per mol equivalent of tertiary butyl alcohol and isobutylene.

The etherification reactor 10 contains a bed of solid etherification catalyst. Any suitable etherification catalyst may be used such as, for example, a solid resin etherification of the type described above, such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

Within the etherification reactor 10, the feed mixture is brought into contact with the bed of an etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reactor is suitably such that about 0.5 to about 20 volumes of feed mixture per volume of etherification catalyst per hour are fed to the etherification reactor 10 and, more preferably from about 1 to about 4 volumes of feed mixture per volume of etherification catalyst per hour.

Within the etherification reactor 10, methanol will exothermically react with the tertiary butyl alcohol and isobutylene to form methyl tertiary butyl ether which will be contained in a reaction product discharged from the etherification reaction zone 10 by way of a line 20 leading to a first methyl tertiary butyl ether (MTBE) distillation zone 30.

The etherification reaction product is charged to the first MTBE distillation zone 30 by way the charge line 20 and is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reaction product 20 is taken overhead from the first distillation zone 30 by a line 32. As a consequence, the first lower boiling distillation fraction 32 taken overhead from the distillation zone 30 will comprise substantially all of the isobutylene and substantially all of the methyl tertiary butyl ether and some of the methanol charged to the first distillation zone 30. The first higher boiling distillation fraction 34 discharged from the first MTBE distillation zone 34 will comprise methanol, tertiary butyl alcohol and water.

The first lighter distillation fraction 32 is continuously charged to a methyl tertiary butyl ether processing zone 40 for the formation of additional methyl tertiary butyl ether from the methanol and isobutylene contained therein and for the recovery of methyl tertiary butyl ether. The methyl tertiary butyl ether is discharged from the methyl tertiary butyl ether processing zone 40 by a line 42 and other reaction products and by-products are discharged by a representative line 44.

The first higher boiling distillation fraction 34 discharged from the first MTBE distillation column 30 is charged to a second tertiary butyl alcohol recovery distillation zone 100 where it is fractionated into a lower boiling distillation fraction discharged in the second distillation zone 100 by a line 112 leading to etherification reactor 10 and a higher boiling distillation fraction comprising water that is discharged from the distillation zone 100 by a line 106.

OPERATION

In accordance with a preferred embodiment of the present invention, a tertiary butyl alcohol charge stock containing from about 95 to 98 wt. % of tertiary butyl alcohol and about 2 to about 5 wt. % of oxygen-containing contaminants including tertiary butyl hydroperoxide, ditertiary butyl peroxide, acetone, methyl formate, tertiary butyl formate, isopropyl alcohol, dimethyl ether, etc., is charged by a line 13 to an oxygenates-decomposition reactor 11 containing a basic zeolite catalyst.

The charge stock is treated under decomposition conditions including a temperature of about 250° to about 500° F., a pressure of about 100 to about 600 psi and a flow rate of about 0.1 to 10 volumes of feedstock per reactor volume per hour to thereby provide a water-containing substantially less-corrosive tertiary butyl alcohol reaction product feedstock comprising a mixture of tertiary butyl alcohol and isobutylene that is substantially free from oxygen-containing contaminants.

The feedstock is discharged from the oxygenates-decomposition reactor 11 by a line 17 leading to etherification reactor 10 containing a bed of a suitable etherification catalyst, such as Amberlyst 15 catalyst. Fresh methanol is continuously charged to etherification reactor 10 by a line 15, as is a recycle stream 112 containing recycle methanol and recycle tertiary butyl alcohol. The flow of methanol and tertiary butyl alcohol to the etherification reactor 10 through the lines 15, 17 and 112 is regulated so that a molar excess of methanol is present in the etherification reactor 10, such as, for example, a molar ratio of about 1.1 to about 3 moles of methanol per mol equivalent of tertiary butyl alcohol and isobutylene. Reaction conditions to be used in the etherification reactor 10 include a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reactor 10 is suitably such that about 0.5 to about 20 volumes of feed mixture per volume of etherification catalyst per hour are fed to the etherification reactor 10 and, more preferably from about 1 to about 4 volumes of feed mixture per volume of etherification catalyst per hour.

The etherification reaction product is discharged from the reactor 10 by a line 20 leading to first methyl tertiary butyl ether distillation zone 30 where the reaction product 20 is separated into a first lower boiling distillation fraction 32 containing isobutylene and methyl tertiary butyl ether and a first higher boiling fraction 34.

The first lower boiling distillation fraction 32 is continuously charged to a methyl tertiary butyl ether processing zone 40 for the formation of additional methyl tertiary butyl ether from the methanol and isobutylene contained therein and for the recovery of methyl tertiary butyl ether. The methyl tertiary butyl ether is discharged from the methyl tertiary butyl ether processing zone 40 by a line 42 and other reaction products and by-products are discharged, as represented by a representative line 44.

The methyl tertiary butyl ether processing zone 40 may be operated in accordance with the manner known to those skilled in the art, as disclosed for example, in Kruse et al. U.S. Pat. No. 5,243,091, Cassata et al. U.S. Pat. No. 5,395,982, Hwan et al. U.S. Pat. No. 5,354,912, etc.

The first higher boiling distillation fraction 34 is discharged from the first MTBE distillation column 30 and is charged to a second tertiary butyl alcohol recovery distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a second lower boiling distillation fraction comprising tertiary butyl alcohol and methanol discharged in the second distillation zone 100 by a line 112 leading to etherification reactor 10 and a second higher boiling distillation fraction comprising water that is discharged from the distillation zone 100 by a line 106.

EXAMPLES

The invention will be further illustrated by the following specific examples which are given by way of illustration, and not as a limitation on the scope of this invention. Where parts are mentioned, they are parts by weight.

EXPERIMENTAL

1. Evaluation of Catalysts

The process of catalytic removal of formates and peroxides was conducted using a fixed-bed downflow reactor made of ⅝" OD×17" long stainless steel tubing. 11 cc of catalyst granules having 20–30 mesh sizes was loaded into the center zone of catalyst bed in the reactor. The feedstock used in the catalyst screening is a tertiary butyl alcohol (TBA) obtained from a TBA Day Tank of a PO/MTBE plant, which contains typically about 0.2–1.2 wt % tertiary butyl formate (TBF) and about 0.1–1.0 wt % organic peroxides.

The catalyst granules were dried at 200°–600° F. for 2 hours in a stream of nitrogen gas at a rate of 50 cc/min prior to contacting with the feed. The liquid feed rate was varied from 11 to 33 cc/min (LHSV=1–3). The feed was pumped under 300 psi back pressure. The TBA feed and nitrogen were mixed and preheated at 120°–180° F. before entering the reactor. The reactor temperature was either held constant while LHSV was varied or raised from 200° to 500° F. when LHSV was fixed at one. The typical test conditions are: nitrogen feed rate 50 cc/min; TBA feed rate 11 cc/min (LHSV=1); 300° F.; and 300 psi. During the 48 hour test period samples of reactor effluent were withdrawn and the compositions were analyzed by gas chromatography.

2. Preparation of Catalysts 2.1 Commercial catalysts

The CBV 3062 ZSM-5, CBV 300-X16 Y, and CBV 20A-X16 mordenite zeolites were used as the supports for the preparation of basic zeolite catalysts.

2.2 Experimental Catalysts

Example I (052-95-6949-017)

Preparation of 10 Wt. % $Cs_2O$ZCBV 3062 ZSM-5 Catalyst 6.6 Grams of cesium hydroxide monohydrate was dissolved in 50 ml of distilled water. Fifty (50) grams of support (05292-2083-000) was impregnated at room temperature then dried at 120° C. for two hours and calcined at 650° C. for five hours.

Example II (052-95-6949-217)

Preparation of 10 Wt. % BaO/ZSM-5

9.25 Grams of barium acetate was dissolved in 50 ml of distilled water. Fifty (50) grams of support was impregnated at room temperature then dried at 120° C. for two hours and calcined at 650° C. for five hours.

Example III (052-95-6949-219)

Preparation of 10 Wt. % BaO/Y Zeolite 9.25 Grams of barium acetate was dissolved in 45 ml of distilled water. Fifty (50) grams of support (052-95- 2542000, CBV 300-X16) was impregnated at room temperature then dried at 120° C. for two hours and calcined at 650° C. for five hours.

Example IV (052-95-6949-019)

Preparation of 10 Wt. % $Cs_2O$/Y Zeolite 6.6 Grams of cesium hydroxide monohydrate was dissolved in 45 ml of distilled water. Fifty (50) grams of support was impregnated at room temperature then dried at 120° C. for two hours and calcined at 650° C. for five hours.

(052-95-6949-119)

IMPREGNATION OF CBV 20A-X16 MORDENITE WITH Cs, Ca AND Ba

SUPPORT: 052-95-2544-000, CBV 20A-X16

10 Wt. % $Cs_2O$ 6.6 Grams of cesium hydroxide monohydrate was dissolved in 45 ml of distilled water. Fifty (50) grams of support was impregnated at room temperature then dried at 120° C. for two hours and calcined at 650° C. for five hours.

EXAMPLE VI (052-95-6949-018)

10 Wt. % CaO 7.35 Grams of calcium hydroxide was dissolved in 45 ml of distilled water and 15 ml of acetic acid. Fifty (50) grams of support was impregnated at room temperature then dried at 120° C. for two hours and calcined at 650° C. for five hours. (052-95-6949-218)

Results and Discussion

Example I is 10% $Cs_2O$ impregnated catalyst on CBV-3062 ZSM-5 zeolite (052-95-6949-017). Table I shows the data summary for Example I at various temperatures. It is seen that as the reactor temperature is increased from 197° to 321° F., the conversion of TBA to isobutylene (i-C4=) goes up from 20.9 to 85.6%. Under the conditions of 321° F., 300 psi, and LHSV=1, the conversions of TBF, DTBP, and TBA are 94.5, 95.1 and 85.6%, respectively. Beyond 321° F., Example I exhibits complete conversions for TBF, DTBP, and TBA.

As the temperature exceeds 286° F., Example I shows 10–20% advantage in TBF removal and 10–80% enhancement in TBA dehydration activity over the alumina catalyst. The data summary for the alumina is presented in Table II.

The influence of metal on the catalytic activities are illustrated by changing to an alkaline earth metal oxide (BaO) from an alkali metal oxide ($Cs_2O$). Example II is 10% BaO impregnated catalyst on CBV-3062 ZSM-5 zeolite (052-95-6949217). The data summary for Example II are given in Table III. It is seen that complete conversions of TBF, DTBP, and TBA can be achieved at a temperature as low as 276° F.

The effect of zeolite structure on the catalyst performance is investigated by using CBV 300-X16 Y zeolite. Example III is 10% BaO impregnated catalyst on V CBV 300-X16 Y zeolite (052-95-6949-219). As shown in Table IV, Example III exhibits greater activities for TBF, DTBP, and TBA conversions than Example II at temperatures lower than 289° F. They are quite comparable at higher temperatures. Under the conditions of 327° F., 300 psi, and LHSV=1, the conversions of TBF, DTBP, and TBA are 100, 97 and 97%, respectively.

Example IV is 10% Cs$_2$O impregnated catalyst on CBV300-X16 Y-zeolite (052-95-6949-019). The performance of Example IV shown in Table V, is very similar to that of Example III. There is no significant difference between Cs and Ba oxide catalysts. The data demonstrates that both alkali metal and alkaline earth metal oxide are suitable for this application.

The performances of 10% Cs$_2$O (Example V) and 10% CaO (Example VI) catalysts supported on mordenite zeolite CBV 20A-X16 are shown in Tables VI and VII, respectively. It is seen that Example V showed high activities in TBA conversion and TBF and DTBP removal at temperatures higher than 313° F. Compared to Example V, the TBA conversion and DTBP removal of Example VI were significantly lower. Therefore, the results illustrate that the extent of dehydration of t-butanol can be controlled by the selection of basic elements. Example V catalyst is more preferred when the process objective calls for a high level of dehydration of t-butanol to make isobutylene.

The results of TBF and DTBP decompositions, and TBA dehydration for Examples I–IV clearly show that the catalysts of this invention are superior to the control catalyst, TK753 alumina. The basic metal oxide catalysts on ZSM-5, Y, and mordenite zeolites can be used in a MTBE synthesis process wherein, in the first step TBA is dehydrated to form isobutylene and the contaminants such as TBF and DTBP are decomposed to gas products, and in the second step isobutylene reacts with methanol to give MTBE. The catalyst of this invention allows the complete TBA dehydration to be achieved at a temperature lower than that required by the prior art alumina catalyst. The catalyst of this invention also permits the complete catalytic decomposition of formate esters and peroxides, thereby, reducing the potential problems of fouling of heater and corrosion of downstream fractionation units.

The process of this invention is distinguished from the prior art technology for hydrogenolysis of formic esters in that no hydrogen is fed into the reactor. The decomposition of and DTBP leads to the formation of non-condensible gas products including CO, CO$_2$, H$_2$ and CH$_4$. The dehydration of TBA gives isobutylene and water. No isobutane was ever detected in the gas products indicating that hydrogenation reaction does not take place in this process. The process chemistry may be best represented as follows:

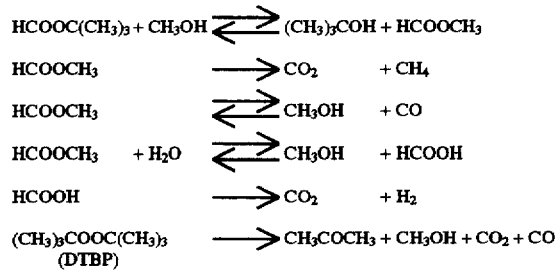

In summary, this invention provides a process for purification of TBA and MTBE streams.

The catalyst of this invention permits the attainment of >90% formate removal and >95% peroxide removal. Large-pore zeolites selected from Y, Beta, mordenite, SAPO-31, SAPO-37 and medium-pore zeolites selected from ZSM-5, ZSM-11 and SAPO-11 zeolite can be used in the instant invention. The desired process temperature, space velocity and pressure are 250°500° F., LHSV=1–10, and 100–600 psi, respectively.

TABLE I

Summary For TBA Dehydration and Contaminants Decomposition Over Cs$_2$O/ZSM-5

Catalyst ID: 052-95-6949-017, 10% Cs$_2$O on CBV-3062, ZSM-5 Zeolite
Run No.: 095-95-0004-000

| Bed Temperature (F.) | TBA Conversion (Wt. %) | TBF Removal (Wt. %) | DTBP Removal (Wt. %) | Weight Percent Recovery (%) |
|---|---|---|---|---|
| 197 | 20.9 | 64.1 | 52.7 | 83.0 |
| 218 | 17.9 | 64.9 | 50.9 | 85.3 |
| 286 | 27.4 | 78.3 | 62.8 | 78.5 |
| 305 | 36.3 | 80.7 | 64.0 | 72.5 |
| 321 | 85.6 | 94.5 | 95.1 | 35.5 |
| 351 | 105.3 | 101.0 | 100.0 | 20.0 |

TABLE II

Summary For TBA Dehydration and Contaminants Decomposition Over TK-753 Alumina Catalyst Catalyst ID: 052-92-2034-000, TK-753 with TBA Feed
Run No.: 095-95-0006-000

| Bed Temperature (F.) | TBA Conversion (Wt. %) | TBF Removal (Wt. %) | DTBP Removal (Wt. %) | Weight Percent Recovery (%) |
|---|---|---|---|---|
| 192 | 52.0 | 95.6 | 69.0 | 59.8 |
| 217 | 12.7 | 68.9 | 48.9 | 88.9 |
| 288 | 7.3 | 63.1 | 66.7 | 92.6 |
| 315 | 13.1 | 69.7 | 78.6 | 88.3 |
| 336 | 12.5 | 83.5 | 87.6 | 88.8 |
| 357 | 11.6 | 72.5 | 96.2 | 89.7 |

TABLE III

Summary For TBA Dehydration and Contaminants Decomposition Over BaO/ZSM-5

Catalyst ID: 052-95-6949-217, 10% BaO on CBV-3062, ZSM-5 Zeolite
Run No.: 094-95-0008-000

| Bed Temperature (F.) | TBA Conversion (Wt. %) | TBF Removal (Wt. %) | DTBP Removal (Wt. %) | Weight Percent Recovery (%) |
|---|---|---|---|---|
| 195 | 25.0 | 51.9 | 35.1 | 80.9 |
| 235 | 33.1 | 83.2 | 35.0 | 75.8 |
| 276 | 100.0 | 100.0 | 100.0 | 11.6 |
| 329 | 100.0 | 100.0 | 100.0 | 19.6 |
| 341 | 98.4 | 100.0 | 100.0 | 25.7 |

TABLE IV

Summary For TBA Dehydration and Contaminants Decomposition Over BaO/Y-Zeolite

Catalyst ID: 052-95-6949-219, 10% BaO on CBV-300-X16, Y-Zeolite
Run No.: 095-95-0005-000

| Bed Temperature (F.) | TBA Conversion (Wt. %) | TBF Removal (Wt. %) | DTBP Removal (Wt. %) | Weight Percent Recovery (%) |
|---|---|---|---|---|
| 197 | 40.2 | 90.3 | 64.6 | 68.8 |
| 242 | 49.3 | 93.7 | 66.8 | 62.5 |
| 289 | 57.1 | 93.0 | 71.3 | 57.4 |

TABLE IV-continued

Summary For TBA Dehydration and Contaminants Decomposition Over BaO/Y-Zeolite

Catalyst ID: 052-95-6949-219, 10% BaO on CBV-300-XI6, Y-Zeolite
Run No.: 095-95-0005-000

| Bed Temperature (F.) | TBA Conversion (Wt. %) | TBF Removal (Wt. %) | DTBP Removal (Wt. %) | Weight Percent Recovery (%) |
|---|---|---|---|---|
| 308 | 84.3 | 96.5 | 85.3 | 36.8 |
| 327 | 97.2 | 101.1 | 97.2 | 26.5 |
| 350 | 100.1 | 100.2 | 100.0 | 24.3 |

TABLE V

Summary For TBA Dehydration and Contaminants Decomposition Over $Cs_2O$/Y-Zeolite

Catalyst ID: 052-95-6949-019, 10% $Cs_2O$ on CBV-300-XI6, Y-Zeolite
Run No.: 095-95-0009-000

| Bed Temperature (F.) | TBA Conversion (Wt. %) | TBF Removal (Wt. %) | DTBP Removal (Wt. %) | Weight Percent Recovery (%) |
|---|---|---|---|---|
| 196 | 38.7 | 84.1 | 54.3 | 70.5 |
| 243 | 53.0 | 92.0 | 64.9 | 59.7 |
| 292 | 57.8 | 86.7 | 66.1 | 56.8 |
| 306 | 86.6 | 95.6 | 87.3 | 34.8 |
| 324 | 100.0 | 100.0 | 100.0 | 11.9 |
| 343 | 100.0 | 100.0 | 100.0 | 15.3 |

TABLE VI

Summary For TBA Dehydration and Contaminants Decomposition Over 10% $Cs_2O$ On CBV 20-X16 Mordenite

Catalyst ID: 10% $Cs_2O$ on CBV 20A-XI6 Mordenite
Run No.: 094-95-0075-000

| Bed Temperature (F.) | TBA Conversion (Wt. %) | TBF Removal (Wt. %) | DTBP Removal (Wt. %) | Weight Percent Recovery (%) |
|---|---|---|---|---|
| 181 | 53.5 | 32.4 | 18.4 | 101.4 |
| 225 | 26.1 | 71.1 | 67.2 | 81.1 |
| 271 | 60.1 | 90.1 | 63.3 | 55.7 |
| 290 | 88.3 | 96.0 | 88.7 | 33.7 |
| 316 | 96.9 | 97.6 | 96.2 | 32.2 |
| 340 | 94.5 | 99.7 | 99.7 | 29.0 |

TABLE VII

Summary For TBA Dehydration and Contaminants Decomposition Over 10% CaO On CBV 20A-X16

Catalyst ID: 10% CaO On CBV 20A-XI6
Run No.: 095-95-0028-000

| Bed Temperature (F.) | TBA Conversion (Wt. %) | TBF Removal (Wt. %) | DTBP Removal (Wt. %) | Weight Percent Recovery (%) |
|---|---|---|---|---|
| 192 | 39.0 | 70.2 | 54.7 | 69.9 |
| 242 | 37.8 | 71.6 | 56.1 | 70.7 |
| 284 | 38.7 | 82.7 | 57.3 | 70.0 |
| 308 | 31.4 | 89.4 | 53.7 | 75.4 |
| 333 | 43.5 | 95.8 | 68.2 | 66.4 |
| 356 | 47.2 | 96.9 | 84.2 | 63.7 |

What is claimed is:

1. A method for the continuous preparation of methyl tertiary butyl ether from tertiary butyl alcohol and methanol which comprises the steps of:

a) continuously feeding a tertiary butyl alcohol charge stock contaminated with from about 0.5 to about 2 wt. % of oxygen-containing impurities, including peroxides and formates to an oxygenates-decomposition reactor containing a basic zeolite catalyst and substantially completely decomposing the oxygen-containing contaminants therein to form a substantially non-corrosive tertiary butyl alcohol feedstock comprising tertiary butyl alcohol and isobutylene that is substantially completely free from peroxide and formate contaminants, b) continuously charging a reaction feed mixture comprising methanol and said non-corrosive tertiary butyl alcohol feedstock to an etherification reactor containing a bed of an etherification catalyst and reacting said reaction feed mixture therein to form a substantially non-corrosive etherification reaction product comprising unreacted methanol, unreacted tertiary butyl alcohol, water, isobutylene and methyl tertiary butyl ether, c) continuously charging said etherification reaction product to a first methyl tertiary butyl ether distillation column and separating it therein into a first lower boiling distillation fraction comprising isobutylene, methanol and methyl tertiary butyl ether and a first higher boiling distillation fraction comprising methanol, tertiary butyl alcohol and water, d) continuously charging said first lower boiling distillation fraction to a methyl tertiary butyl ether processing zone for the formation of additional methyl tertiary butyl ether from the methanol and isobutylene contained therein and for the recovery of methyl tertiary butyl ether;

e) continuously charging said first higher boiling distillation fraction to a second tertiary butyl alcohol recovery distillation column and separating it therein into a second lower boiling tertiary butyl alcohol recycle fraction and a second higher boiling water fraction; and f) continuously recycling the second lower boiling tertiary butyl alcohol recycle fraction to the etherification reactor.

2. A method as in claim 1 wherein the reaction conditions in the oxygenates decomposition reactor include a temperature of about 250° to about 500° F., a pressure of about 100 to about 600 psi and a flow rate of about 0.1 to 10 volumes of feedstock per reactor volume per hour.

3. A method as in claim 2 wherein the catalyst in the oxygenates decomposition reactor is a basic zeolite catalyst having about 1 to about 15 wt. % of an alkali metal or alkaline earth metal oxide deposited thereon.

4. A method as in claim 3 wherein barium oxide is deposited on the zeolite.

5. A method as in claim 3 wherein calcium oxide is deposited on the zeolite.

6. A method as in claim 3 wherein cesium oxide is deposited on the zeolite.

7. A method for the continuous preparation of methyl tertiary butyl ether from tertiary butyl alcohol and methanol which comprises the steps of:

a) continuously feeding a corrosive tertiary butyl alcohol charge stock contaminated with from about 0.5 to about 2 wt. % of oxygen-containing impurities, including peroxides and formates to an oxygenates-decomposition reactor containing a basic zeolite catalyst and substantially completely decomposing the oxygen-containing contaminants therein under reaction conditions including a temperature of about 250° to about 500° F., a pressure of about 100 to about 600 psi and a flow rate of about 0.1 to 10 volumes of feedstock per reactor volume per hour to form a less corrosive tertiary butyl alcohol feedstock comprising tertiary butyl alcohol and isobutylene that is substantially completely free from peroxide and formate contaminants, said basic zeolite catalyst having about 1 to about 15 wt. % of an alkali metal or alkaline earth metal oxide deposited thereon.

8. A method as in claim 7 wherein barium oxide is deposited on the zeolite.

9. A method as in claim 7 wherein calcium oxide is deposited on the zeolite.

10. A method as in claim 7 wherein cesium oxide is deposited on the zeolite.

* * * * *